United States Patent
Moaddeb et al.

(10) Patent No.: US 7,594,887 B2
(45) Date of Patent: *Sep. 29, 2009

(54) SHAPE MEMORY DEVICES AND METHODS FOR RESHAPING HEART ANATOMY

(75) Inventors: Shahram Moaddeb, Irvine, CA (US); Samuel M. Shaolian, Newport Beach, CA (US); Emanuel Shaoulian, Corona Del Mar, CA (US); Richard Rhee, Anaheim, CA (US); Steven C. Anderson, Rancho Santa Margarita, CA (US)

(73) Assignee: MiCardia Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/876,586

(22) Filed: Oct. 22, 2007

(65) Prior Publication Data

US 2008/0039681 A1 Feb. 14, 2008

Related U.S. Application Data

(63) Continuation of application No. 11/142,078, filed on May 31, 2005, now Pat. No. 7,285,087.

(60) Provisional application No. 60/588,254, filed on Jul. 15, 2004.

(51) Int. Cl.
*A61F 2/02* (2006.01)
(52) U.S. Cl. ...................................................... 600/37
(58) Field of Classification Search .................. 600/37; 128/897, 898; 606/151–156
See application file for complete search history.

(56) References Cited

U.S. PATENT DOCUMENTS

| 5,052,300 A | 10/1991 | Josse |
| 5,176,618 A | 1/1993 | Freedman |

(Continued)

OTHER PUBLICATIONS

Calo-Mer, Shape-Memory Thermoplastic [online], Apr. 8, 2003 [retrieved on May 18, 2005]. Retrieved from the Internet: <URL:http:/www.polymertech.com/materials/calomer.html>, 4 pages.

(Continued)

*Primary Examiner*—Samuel G Gilbert
(74) *Attorney, Agent, or Firm*—Aaron D. Barker; Stoel Rives LLP

(57) ABSTRACT

Systems, methods and devices are provided for treating heart failure patients suffering from various levels of heart dilation. Such heart dilation is treated by reshaping the heart anatomy with the use of shape memory elements. Such reshaping changes the geometry of portions of the heart, particularly the right or left ventricles, to increase contractibility of the ventricles thereby increasing the stroke volume which in turn increases the cardiac output of the heart. The shape memory elements have an original shape and at least one memory shape. The elements are implanted within the heart tissue or attached externally and/or internally to a surface of the heart when in the original shape. The elements are then activated to transition from the original shape to one of the at least one memory shapes. Transitioning of the elements cause the associated heart tissue areas to readjust position, such as to decrease the width of the ventricles. Such repositioning is maintained over time by the elements, allowing the damaging effects of heart dilation to slow in progression or reverse.

14 Claims, 13 Drawing Sheets

U.S. PATENT DOCUMENTS

| | | | |
|---|---|---|---|
| 5,979,456 | A | 11/1999 | Magovern |
| 6,110,100 | A * | 8/2000 | Talpade .................... 600/37 |
| 6,123,724 | A | 9/2000 | Denker |
| 6,160,084 | A | 12/2000 | Langer et al. |
| 6,165,122 | A | 12/2000 | Alferness |
| 6,174,279 | B1 | 1/2001 | Girard |
| 6,193,648 | B1 | 2/2001 | Krueger |
| 6,332,863 | B1 | 12/2001 | Schweich, Jr. et al. |
| 6,332,864 | B1 | 12/2001 | Schweich, Jr. et al. |
| 6,388,043 | B1 | 5/2002 | Langer et al. |
| 6,402,679 | B1 | 6/2002 | Mortier et al. |
| 6,416,459 | B1 | 7/2002 | Haindl |
| 6,540,666 | B1 | 4/2003 | Chekanov |
| 6,567,699 | B2 | 5/2003 | Alferness et al. |
| 6,587,734 | B2 | 7/2003 | Okuzumi |
| 6,595,912 | B2 | 7/2003 | Lau et al. |
| 6,602,184 | B2 | 8/2003 | Lau et al. |
| 6,604,529 | B2 | 8/2003 | Kim |
| 6,612,979 | B2 | 9/2003 | Lau et al. |
| 6,622,979 | B2 | 9/2003 | Valiulis |
| 6,629,921 | B1 | 10/2003 | Schweich et al. |
| 6,645,139 | B2 | 11/2003 | Haindl |
| 6,663,558 | B2 | 12/2003 | Lau et al. |
| 6,673,009 | B1 | 1/2004 | Vanden Hoek et al. |
| 6,682,474 | B2 | 1/2004 | Lau et al. |
| 6,689,048 | B2 | 2/2004 | Vanden Hoek et al. |
| 6,702,732 | B1 | 3/2004 | Lau et al. |
| 6,720,402 | B2 | 4/2004 | Langer et al. |
| 6,723,038 | B1 | 4/2004 | Schroeder et al. |
| 6,723,041 | B2 | 4/2004 | Lau et al. |
| 6,746,471 | B2 | 6/2004 | Mortier et al. |
| 6,755,777 | B2 | 6/2004 | Schweich, Jr. et al. |
| 6,755,779 | B2 | 6/2004 | Vanden Hoek et al. |
| 6,776,784 | B2 * | 8/2004 | Ginn .................... 606/151 |
| 7,285,087 | B2 * | 10/2007 | Moaddeb et al. .............. 600/37 |
| 2002/0065373 | A1 | 5/2002 | Krishnan |
| 2002/0161114 | A1 | 10/2002 | Gunatillake et al. |
| 2002/0188170 | A1 * | 12/2002 | Santamore et al. ............ 600/37 |
| 2003/0078671 | A1 | 4/2003 | Lesnlak et al. |
| 2003/0199974 | A1 | 10/2003 | Lee et al. |
| 2003/0233045 | A1 | 12/2003 | Vaezy |
| 2004/0002626 | A1 | 1/2004 | Feld et al. |
| 2004/0014929 | A1 | 1/2004 | Lendlein et al. |
| 2004/0015187 | A1 | 1/2004 | Lendlein et al. |
| 2004/0098121 | A1 | 5/2004 | Opolski |
| 2004/0116945 | A1 | 6/2004 | Sharkawy et al. |
| 2004/0149290 | A1 | 8/2004 | Nelson et al. |
| 2004/0234453 | A1 | 11/2004 | Smith |
| 2004/0260393 | A1 | 12/2004 | Rahdert et al. |
| 2006/0015003 | A1 | 1/2006 | Moaddes et al. |

OTHER PUBLICATIONS

Cohen-Karni et al., "Fe-Pd Alloy Ferromagnetic Shape Memory Thin Films," Research Experience for Undergraduates Project, Harvard University, 2003, 31 pages.

Lendlein et al., Biodegradable, Elastic Shape-Memory Polymers for Potential Biomedical Applications, Science, vol. 296 (May 31, 2002), pp. 1673-1676.

Li, Studies on Thermally Stimulated Shape Memory Effect of Segmented Polyurethanes, J Appl Plym Sci, (1997) 64: 1511-1516.

Oikawa, Development of Co-Ni-Al-based Ferromagnetic Shape Memory Alloys, AIST Today, vol. 1, No. 7 (2001), pp. 18.

Tellinen et al., "Basic Properties of Magnetic Shape Memory Actuators," Published in 8th International Conference Actuator, Bremen, Germany, Jun. 2002, pp. 10-12.

Office Action mailed Dec. 14, 2006, for U.S. Appl. No. 11/142,127, filed May 31, 2005.

Office Action mailed Jun. 4, 2007, for U.S. Appl. No. 11/142,127, filed May 31, 2005.

Office Action mailed Jul. 11, 2007, for U.S. Appl. No. 11/142,127, filed May 31, 2005.

Office Action mailed Jan. 9, 2007, for U.S. Appl. No. 11/142,078, filed May 31, 2005.

* cited by examiner

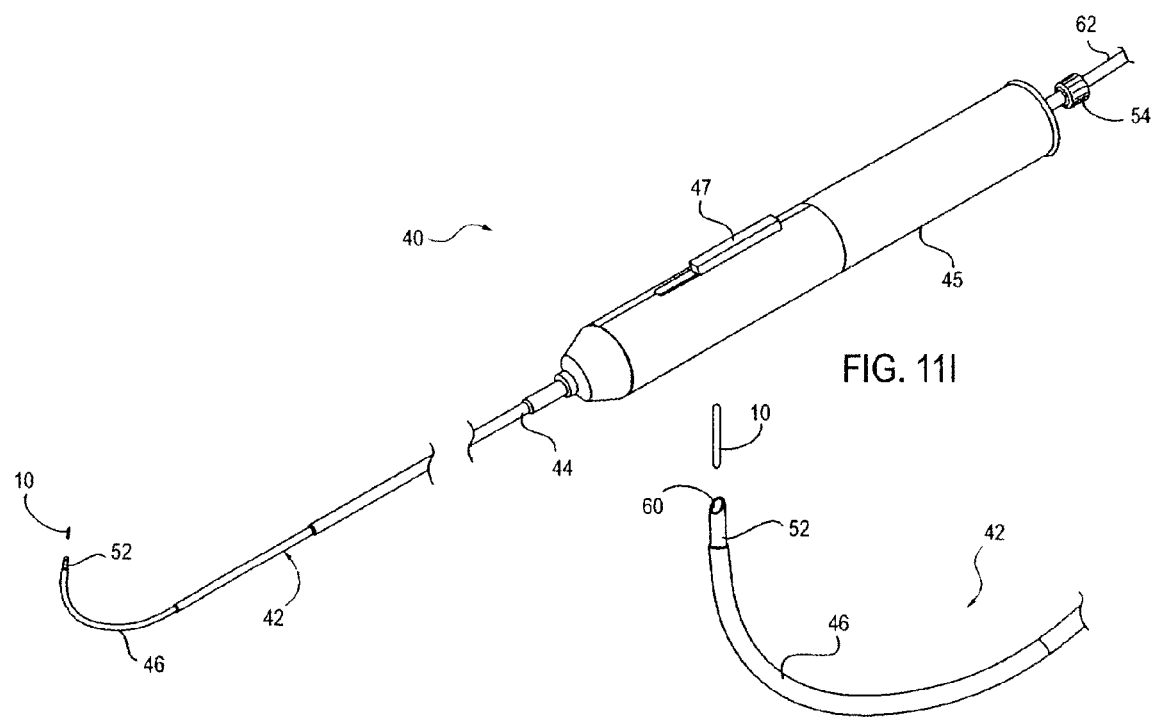

SHAPE MEMORY DEVICES AND METHODS FOR RESHAPING HEART ANATOMY

CROSS-REFERENCES TO RELATED APPLICATIONS

This application is a continuation of U.S. patent application Ser. No. 11/142,078, filed May 31, 2005, which claims the benefit of U.S. Provisional Patent Application No. 60/588,254, filed Jul. 15, 2004, both of which are hereby incorporated by reference for all purposes.

This application is also related to U.S. patent application Ser. No. 11/142,127, filed May 31, 2005 and incorporated herein by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure, many of which are not fully known. In certain instances, heart disease may result from viral infections. In such cases, the heart may enlarge to such an extent that the adverse consequences of heart enlargement continue after the viral infection has passed and the disease continues its progressively debilitating course. In other cases, the initial cause is due to chronic hypertension, myocardial infarction, mitral valve incompetency, or other dilated cardiomyopathies. With each of these conditions, the heart is forced to overexert itself in order to provide the cardiac output demanded by the body during its various demand states. The result is dilation of the left ventricle and remodeling of the heart tissues.

Remodeling involves physical changes to the size, shape and thickness of the heart wall along with a neurohormonal milieu of the entire cardiovascular system. A damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. If dilation exceeds a critical value, the result will be progressive heart dilation which can be explained by Laplace's law. As the volume subtended by the left hear chamber increases, the stresses in the walls of this cavity will increase. Consequently, the muscle fibrils are overloaded and their ideal range of elongation is exceeded. When this excessive elongation takes place, there is a residual volume in the heart. Then the muscle fibrils must operate against a primarily high wall strain, and are further extended. A vicious cycle arises, leading to increasing distension of the heart and consequent heart insufficiency.

Heart transplantation is one surgical procedure used for treatment of heart failure. Unfortunately, not enough hearts are available for transplant to meet the needs of heart failure patients. In the United States, in excess of 35,000 transplant candidates compete for only about 2,000 transplants per year. A transplant waiting list is about 8-12 months long on average and frequently a patient may have to wait about 1-2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Consequently, substantial effort has been made to find alternative treatments for heart failure. One such surgical treatment is referred to as the Batista procedure; the surgical technique includes dissecting and removing portions of the heart in order to reduce heart volume. This is a radical and experimental procedure subject to substantial controversy. Furthermore, the procedure is highly invasive, risky and expensive and commonly includes other expensive procedures (such as a concurrent heart valve replacement). And if the procedure fails, emergency heart transplant is the only available option.

Another surgical treatment is dynamic cardiomyoplasty. In this procedure, the latissimus dorsi muscle (taken from the patient's shoulder) is wrapped around the heart and chronically paced synchronously with ventricular systole. Pacing of the muscle results in muscle contraction to assist the contraction of the heart during systole. Even though cardiomyoplasty has demonstrated symptomatic improvement, studies suggest the procedure only minimally improves cardiac performance. In addition, the procedure is highly invasive requiring harvesting a patient's muscle and an open chest approach (i.e., sternotomy) to access the heart. Furthermore, the procedure is expensive, especially for those using a paced muscle which require costly pacemakers. The cardiomyoplasty procedure is also complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

A variety of devices have also been developed to treat heart failure by improving cardiac output. For example, left ventricular assist pumps have been developed to help the heart to pump blood. These mechanical pumps reduce the load on the heart by performing all or part of the pumping function normally done by the heart. Currently, mechanical pumps are used to sustain the patient while a donor heart for transplantation becomes available for the patient. Researchers and cardiac surgeons have also experimented with prosthetic "girdles" disposed around the heart. One such design is a prosthetic "sock" or "jacket" that is wrapped around the heart.

However, these designs require invasive open chest surgery, significant handling of the heart, and have not seen widespread success.

Consequently, there is a need for alternative treatments applicable to both early and later stages of heart failure to correct pumping insufficiency due to distension of the heart thereby stopping the progressive nature of the disease or more drastically slowing the progressive nature of congestive heart disease. It is also desired that such therapies require minimal manipulation of the heart, be available to a broad spectrum of patients with various degrees of heart failure, be cost effective, safe and efficient. At least some of these objectives will be met with the present invention.

BRIEF SUMMARY OF THE INVENTION

Systems, methods and devices are provided for treating heart failure patients suffering from various levels of heart dilation. Such heart dilation is treated by reshaping the heart anatomy with the use of shape memory elements. Such reshaping changes the geometry of portions of the heart, particularly the right or left ventricles, to increase contractibility of the ventricles thereby increasing the stroke volume which in turn increases the cardiac output of the heart. The shape memory elements have an original shape and at least one memory shape. The elements are implanted within the heart tissue or attached externally and/or internally to a surface of the heart when in the original shape. The elements are then activated to transition from the original shape to one of the at least one memory shapes. Transitioning of the elements cause the associated heart tissue areas to readjust position, such as to decrease the width of the ventricles. Such repositioning is maintained over time by the elements, allowing the damaging effects of heart dilation to slow in progression or reverse.

In a first aspect of the present invention, a device for reshaping the heart anatomy is provided. In preferred embodiments, the device comprises a shape memory element which is transitionable between an original shape and at least one memory shape, wherein the original shape is configured for at least partial implantation within a tissue area of the heart anatomy and the at least one memory shape is configured to apply force to the tissue area in a manner which reshapes the heart anatomy. In some embodiments, the shape memory element undergoes a deformation of at least 100% in the transition, however it may be appreciated that in some embodiments more than 100% deformation is achieved, such as several hundred percent. Further, in some embodiments, the transition substantially occurs within up to approximately 35 seconds. Such a relatively quick transition time provides advantages such as shorter procedure time and ease of use.

It may be appreciated that the original shape and the at least one memory shape may have a variety of forms, including straight, curved, curled, folded, expanded, compressed, bumped, jagged, or looped, to name a few. Generally shapes which are not straight are considered curved. Thus, in some embodiments the at least one memory shape has a more curved configuration than the original shape. In these instances, such increase in curvature applies force to the tissue area in a manner which reshapes the heart anatomy. It may be appreciated that the opposite may also be the case, in which the at least one memory shape has a less curved configuration than the original shape. In these instances, such decrease in curvature applies force to the tissue area in a manner which reshapes the heart anatomy. Preferably, the tissue area is located within a wall of a ventricle so that the at least one memory shape is configured to apply force to the tissue area in a manner which reduces a width of the ventricle. It may be appreciated that the walls of the ventricle include the septal wall. The at least one shape memory element is typically transitionable in response to a change in temperature, application of light, change in ionic concentration, a change in pH, application of an electric field, application of a magnetic field, application of ultrasound or a combination of these.

In preferred embodiments, the shape memory element comprises at least one shape memory polymer. The at least one shape memory polymer may comprise a hard segment and at least one soft segment, wherein the hard segment has a transition temperature which is higher than transition temperatures of the at least one soft segment. Likewise, the at least one shape memory polymer may comprise a hard segment and more than one soft segment, wherein the hard segment has a transition temperature which is higher than a transition temperature of one of the soft segments and each subsequent soft segment has a transition temperature which is lower than a preceding soft segment.

In other embodiments, the shape memory element comprises at least one shape memory metal or metal alloy. Typically, the at least one shape memory metal or metal alloy has a thermoelastic martensitic transition temperature. Examples of such shape memory metal alloys include Ti—Ni alloys, Cu—Zn—Al alloys, Cu—Al—Ni alloys, Fe—Ni—Al alloys, or a combination of these. In other embodiments, the at least one shape memory metal or metal alloy exhibits a paramagnetic or ferromagnetic transition. Examples of such shape memory metal alloys include Fe—C, Fe—Pd, Fe—Mn—Si, Co—Mn, Fe—Co—Ni—Ti, $Ni_2MnGa$, Co—Ni—Al, Ni—Mn—Ga, or a combination of these.

In some embodiments, the shape memory element includes at least one coating or covering. For example, the coating or covering may comprise a biocompatible material, such as poly tetra fluoro ethylene, fluorinated ethylene propylene, poly ether ether ketone, or a combination of these. Or, the coating may comprise a magnetic resonance imaging absorbing coating or a high intensity focused ultrasound absorbing coating. Further, the covering may comprise at least one fine conductive wire. It may be appreciated that the at least one coating or covering may comprise a plurality of coatings or coverings wherein at least one coating or covering is different from the other coating(s) or covering(s).

In a second aspect of the present invention, a method of reshaping heart anatomy is provided. In preferred embodiments, the method includes providing a shape memory element which is transitionable between an original shape and at least one memory shape, implanting the shape memory element having its original shape at least partially within a tissue area of the heart anatomy, and activating the shape memory element causing transition from its original shape to one of the at least one memory shapes while the element is at least partially implanted, wherein the transition causes the tissue area to move in a manner which reshapes the heart anatomy. Typically, the tissue area is located within a wall of a ventricle and reshaping the heart anatomy comprises reducing a width of the ventricle. And, activating may comprise providing a change in temperature, application of light, change in ionic concentration, a change in pH, application of an electric field, application of a magnetic field, application of ultrasound or a combination of these.

As stated above, the shape memory element may comprise at least one shape memory polymer. In particular, the at least one shape memory polymer may comprises a hard segment and at least one soft segment, wherein the hard segment has a transition temperature which is higher than transition temperatures of the at least one soft segment. In such instances, activating may comprise raising the temperature of the at least one shape memory polymer through at least one of the transition temperatures.

When the shape memory element comprises at least one shape memory metal or metal alloy having a transition temperature, activating may comprises raising the temperature of the at least one shape memory metal or alloy through its transition temperature. Similarly, when the shape memory element comprises at least one shape memory metal or metal alloy having a thermoelastic martensitic transition temperature, activating may comprise raising the temperature of the at least one shape memory metal or alloy through the thermoelastic martensitic transition temperature. Likewise, when the shape memory element comprises at least one shape memory metal or metal alloy capable of exhibiting a paramagnetic or ferromagnetic transition, activating may comprise applying a magnetic field to the metal or metal alloy. Also, when the shape memory element includes a coating comprising a magnetic resonance imaging absorbing coating, activating the shape memory element may comprise applying a magnetic field to the magnetic resonance imaging absorbing coating.

In some embodiments, the shape memory element includes a coating or covering. When the coating or covering comprises an ultrasound absorbing coating, activating the shape memory element may comprise applying ultrasound to the ultrasound absorbing coating. When the covering comprises at least one fine conductive wire, activating the shape memory element comprises applying thermal energy to the at least one fine conductive wire.

In some embodiments, implanting comprises positioning the shape memory element at least partially on a surface of the heart anatomy, such as an internal or external surface of a ventricle. In some instances, the shape memory element includes portions which penetrate the tissue and portions which remain on the surface of the tissue, such as in a staple-like fashion. Other times implanting comprises stitching the shape memory element through the tissue area, such as in a sewing motion. Other methods of at least partially implanting may be used. Such methods are in addition to implanting the shape memory element completely within the tissue or attaching the shape memory element to a surface of the tissue.

Other objects and advantages of the present invention will become apparent from the detailed description to follow, together with the accompanying drawings.

BRIEF DESCRIPTION OF THE DRAWINGS

FIGS. 11A-11J illustrates an embodiment of a delivery system.

DETAILED DESCRIPTION OF THE INVENTION

Figure 1:
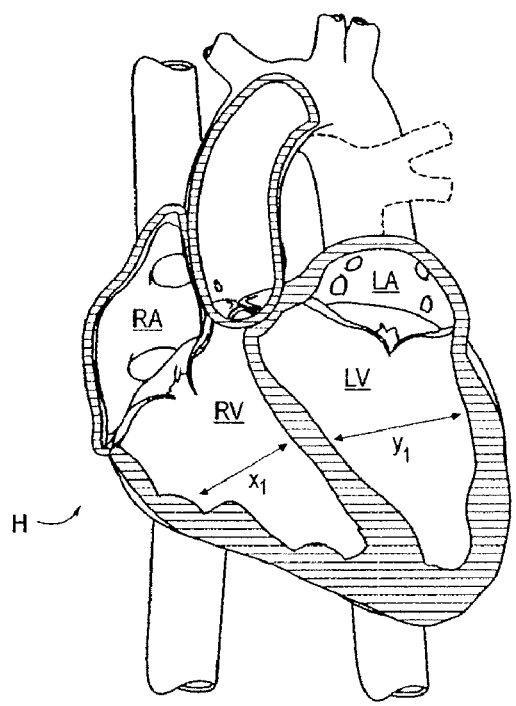
FIG. 1 provides a cross-sectional illustration of a heart of a normal patient.
Figure 2:
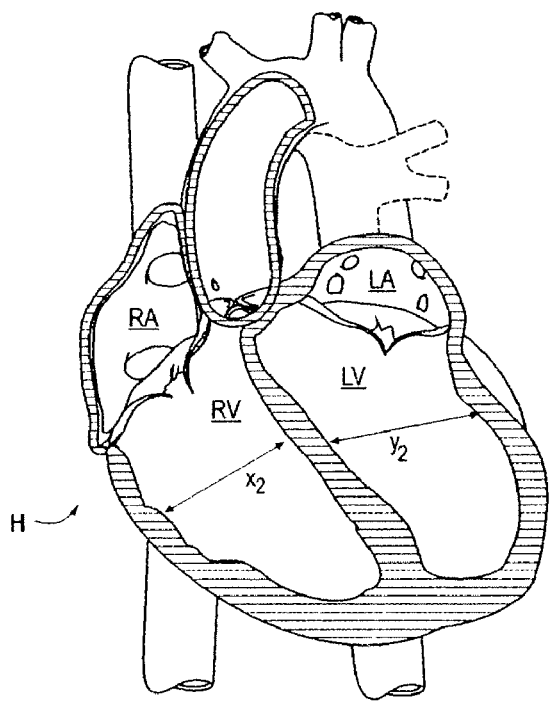
FIG. 2 provides a cross-sectional illustration of a heart of a patient wherein the geometry of the ventricles have dilated.

FIG. 1 provides a cross-sectional illustration of a heart H of a normal patient. The cross-sectional view shows the right atrium RA, right ventricle RV, left atrium LA and left ventricle LV. The right ventricle RV and left ventricle LV have a width of $x_1$ and $y_1$ respectively. FIG. 2 provides a cross-sectional illustration of a heart H of a patient with heart disease wherein the geometry of the ventricles RV, LV have dilated. As shown, the right ventricle RV and left ventricle LV have increased widths of $x_2$ and $y_2$ respectively. The increased widths $x_2$, $y_2$ result in poor cardiac output from the left ventricle LV and/or the right ventricle RV. Cardiac output (CO) is defined as:

$$CO = HR \times SV$$

whereas
HR=heart rate (beats per minute)
SV=stroke volume (liters per beat)
Ejection Fraction (EF) is the fraction of blood ejected by a ventricle relative to its end-diastolic volume. Therefore, EF is calculated from:

$$EF = (SV/EDV) * 100$$

whereas
EDV=end-diastolic volume
Ejection fraction is most commonly measured using echocardiography. This non-invasive technique provides good estimates of end-diastolic (EDV) and end-systolic volumes (ESV), and stroke volume (SV=EDV−ESV). Normally, EF is >60%. For example, if the SV is 75 ml and the EDV is 120 ml, then the EF is 63%. Factors effecting EDV are heart rate, ventricular compliance and filling pressure. Factors effecting ESV are the force of contracting the left ventricle and after-load which is the measure of the force resulting from the ejection of blood.

In heart failure, particularly in dilated cardiomyopathy, EF can become very small as SV decreases and EDV increases. In severe heart failure, EF may be only 20%. EF is often used as a clinical index to evaluate the status of the heart. By changing the geometry or reshaping the left or right ventricle with the methods and devices of the present invention, the contractibility of the ventricles may be increased thereby increasing the stroke volume (SV). This in turn increases the cardiac output (CO).

The geometry of the ventricles are changed by placing shape memory elements on or within tissue areas or walls of the ventricles. The shape memory elements are comprised of a shape-memory material. A variety of shape-memory materials may be used and will be described in detail in later sections. In general, however, shape memory is the ability of a material to revert to at least one shape held in its memory when actuated by an environmental change. Examples of such environmental changes include changes in temperature, application of light, changes in ionic concentration and/or pH, or application of an electric field, magnetic field or ultrasound, to name a few. The material can also typically resume its original shape by return of the environmental condition, thus having a two-way effect.

Figure 3A:
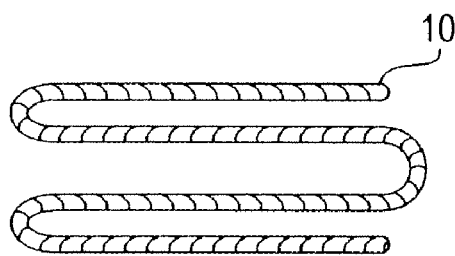
FIGS. 3A-3B illustrate a shape memory element holding an original compressed folded shape and a memory expanded folded shape.
Figure 3B:
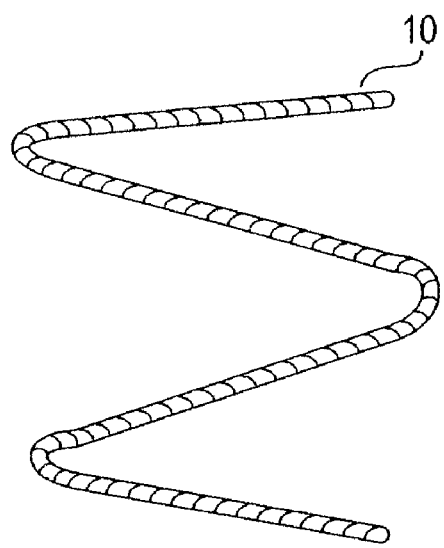

FIGS. 3A-3B illustrate a shape memory element 10 holding two different shapes, an original shape (FIG. 3A) and a memory shape (FIG. 3B). The element 10 has the original shape in a common environment, in this instance a compressed folded shape, and maintains the memory shape, in this instance an expanded folded shape, in its memory. The element 10 can be used in a variety of manners while in the original shape, in anticipation of reverting the element 10 to its memory shape at a future time. Optionally, the element 10 could additionally be reverted back to its original shape at yet another future time.

Figure 4A:
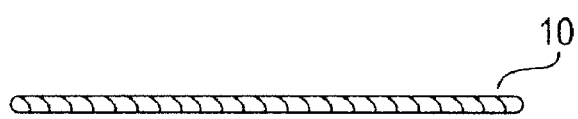
FIGS. 4A-4B illustrate a shape memory element holding an original straight shape and a memory folded shape.
Figure 4B:
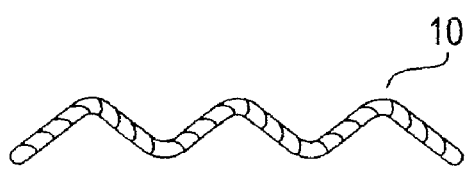
Figures 5A, 5B:
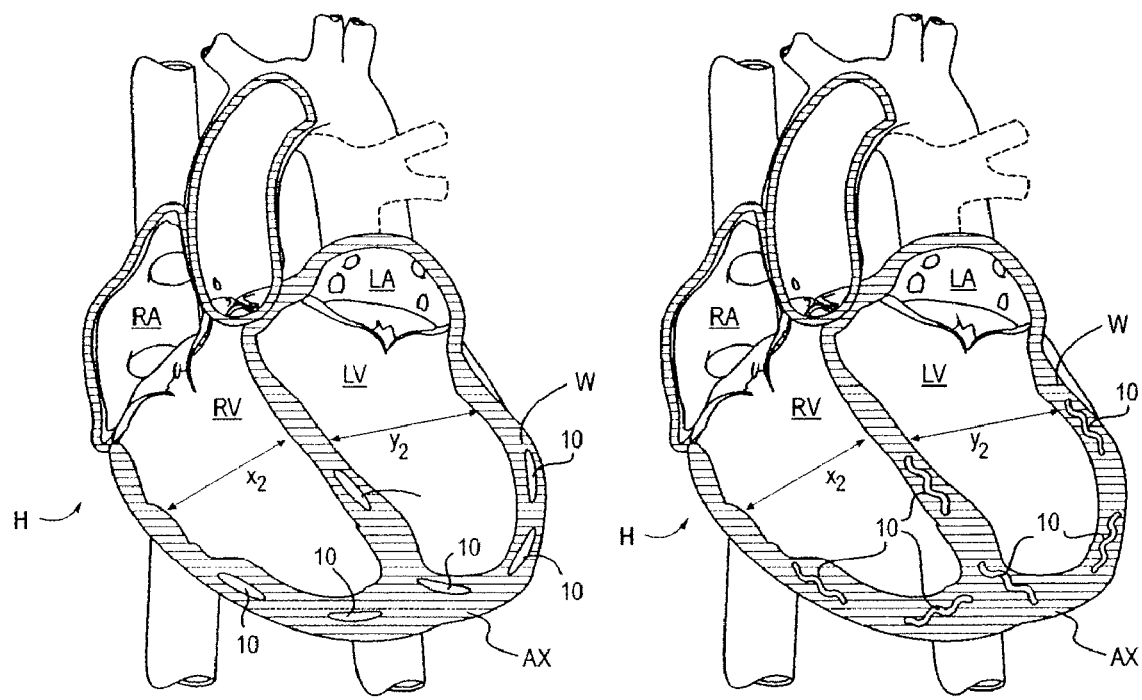
FIG. 5A illustrates shape memory elements in their original straight shape implanted within walls of the heart.
FIG. 5B illustrates the shape memory elements of FIG. 5A transitioned to their memory folded shape while implanted within the walls of the heart.

Similarly, FIGS. 4A-4B illustrate a shape memory element 10 holding two different shapes, an original shape (FIG. 4A) and a memory shape (FIG. 4B). The element 10 has the original shape in the common environment, in this instance a straight shape, and maintains the memory shape, in this instance a folded shape, in its memory. The element 10 may have the form of a rod or ribbon structure, and, in some embodiments, have a diameter in the range of approximately 0.25-0.5 mm and a thickness in the range of approximately 0.05-0.1 mm. Referring to FIG. 5A, the shape memory elements 10 in their original straight shape may be implanted within the walls W of the right ventricle RV and left ventricle LV near the apex AX of the heart H. As shown, the ventricles RV, LV are expanded and have widths $x_2$ and $y_2$ respectively. The shape memory elements 10 may then be reverted to their memory folded shape, FIG. 5B, by application of an environmental factor, such as a temperature change, a magnetic field, etc. Upon application, the elements 10 begin to fold and retract, drawing the tissue of the ventricle walls together in a contracted fashion. This in turn reshapes the ventricles RV, LV toward their normal width $x_1$ and width $y_1$, respectively. The shape changes of the ventricles RV, LV increase the contractibility of the ventricles RV, LV. This increases the stroke volume (SV) which increases the cardiac output (CO).

Figure 6A:
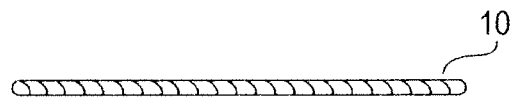
FIGS. 6A-6B illustrate a shape memory element holding an original straight shape and a memory curved shape.
Figure 6B:
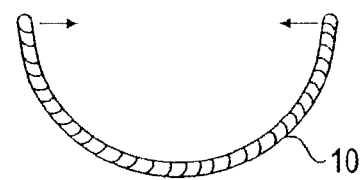
Figure 6C:
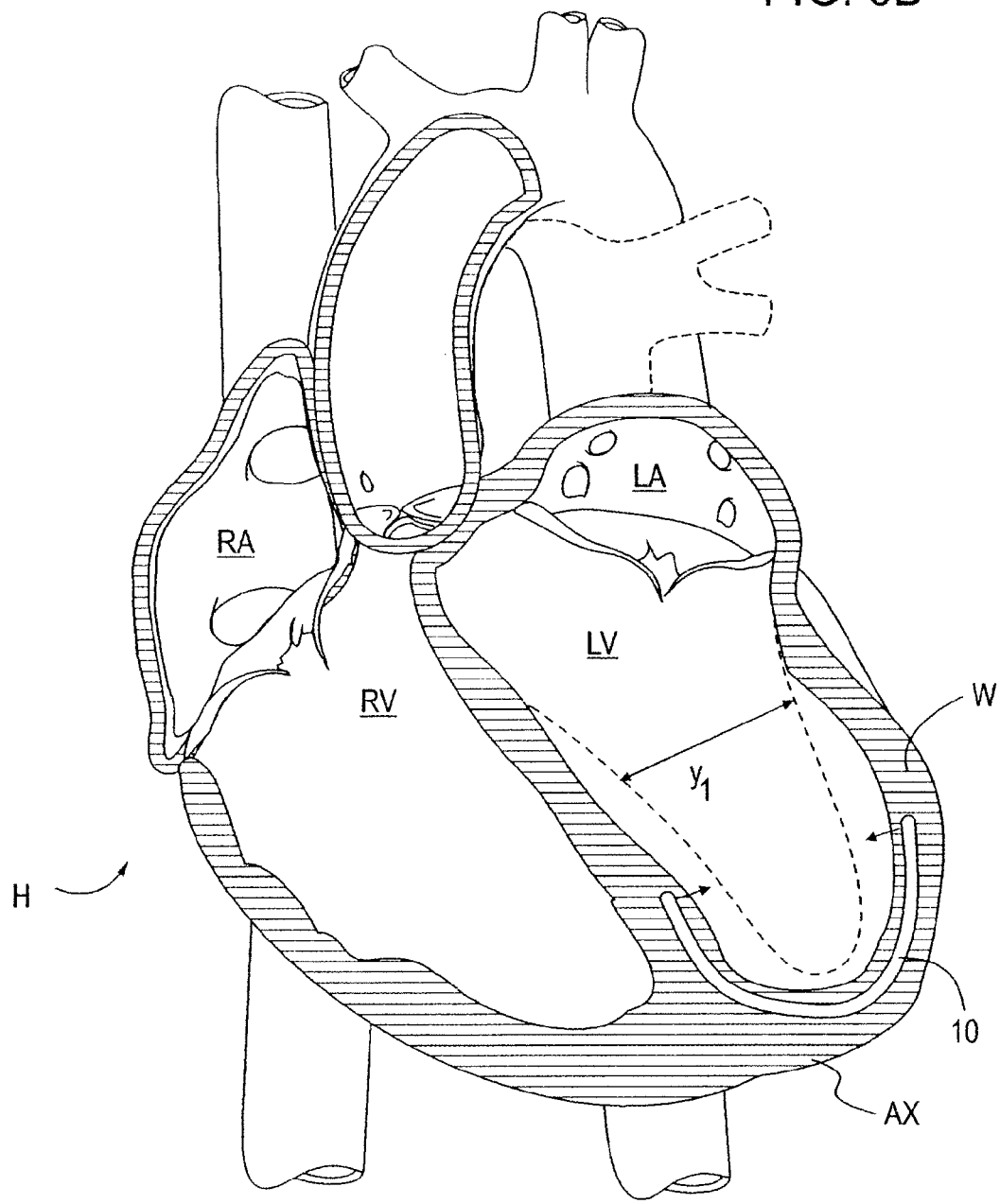
FIG. 6C illustrates the shape memory element of FIGS. 6A-6B implanted within the wall of the heart.

Further, FIGS. 6A-6B illustrate a shape memory element 10 holding two different shapes, an original shape (FIG. 6A) and a memory shape (FIG. 6B). The element 10 has the original shape in the common environment, in this instance a straight shape, and maintains the memory shape, in this instance a curved shape, in its memory. Referring to FIG. 6C, a shape memory element 10 in its original straight shape may be implanted within the walls W of a ventricle, such as the left ventricle LV as shown. Due to its positioning along the apex AX of the heart H, the element 10 takes on a slight curvature. The element 10 may then be reverted to its memory curved shape of FIG. 6B by application of an environmental factor, such as a temperature change, a magnetic field, etc. Upon application, the element 10 begins to curve inwardly as indicated by arrows. Such curving draws the walls W of the left ventricle LV inward, toward each other, thereby reshaping the left ventricle LV. The width of the left ventricle LV is thus reduced toward the normal width $y_1$. The shape change of the ventricle LV increases the contractibility of the ventricle LV. This increases the stroke volume (SV) which increases the cardiac output (CO).

It may be appreciated that the implanted elements 10 may vary by original shape, memory shape, length, width, size, material, environmental actuation factor, and rate or extent of change, to name a few. Further, the elements 10 may be actuated at the same or varied times. Likewise, the elements 10 may remain in their memory shape or be reverted toward their original shape at any time, and at the same or varied times. This may be repeated any number of times.

It may also be appreciated that any number of elements 10 may be used and the elements 10 may be positioned at any location on (externally or internally) or within the walls W of the heart H, including the right atrium RA, right ventricle RV, left atrium LA and left ventricle LV, which includes the septal wall. It may further be appreciated the elements 10 may be positioned on or within the valves, including the mitral valve MV, aortic valve AV, tricuspid valve TV, and pulmonary valve (not shown), and/or any of the associated anatomy, such as the aorta A, pulmonary artery, pulmonary vein, chordae etc. Further, the elements 10 may be positioned at one area to change the shape of a different area. For example, elements 10 may be positioned within the left atrium LA to change the shape of the mitral valve MV. In some embodiments, one or more elements are positioned within the coronary sinus to change the shape of the mitral valve annulus. The coronary sinus is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. One or more elements 10 may be introduced into the coronary sinus and then activated to change shape which in turn reshapes and advantageously effects the geometry of the mitral valve annulus.

Figure 7A:
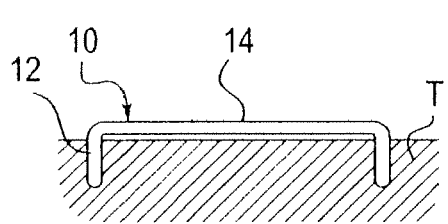
FIGS. 7A-7B illustrate a shape memory element having a staple-like original shape.
Figure 7B:
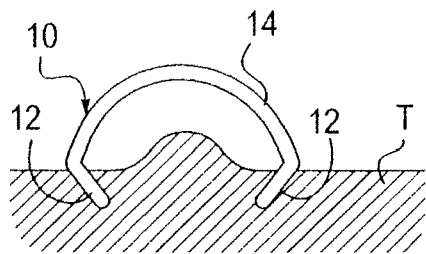

It may also be appreciated that the shape memory elements 10 may be fully implanted, partially implanted or otherwise attached to the tissues of the heart. For example, as shown in FIG. 7A, an element 10 may have a staple-like original shape having a two prongs 12 which are penetrable into tissue T and are connected by a straight portion 14 which resides above or on the surface of the tissue T. Upon activation, the element 10 changes to its memory shape, as shown in FIG. 7B. Here, the straight portion 14 bends or curves, directing the prongs 12 toward each other along with the associated tissue T. Such a shape memory element 10 may be used on any surface (external or internal) of the heart or related anatomy to plicate or otherwise draw tissue together. It may be appreciated that the shapes may be reversed, i.e. the original shape being the curved shape of FIG. 7B and the memory shape being the staple-like shape of FIG. 7A. In such instance, the element 10 may be used to extend tissue segments.

Figure 8A:
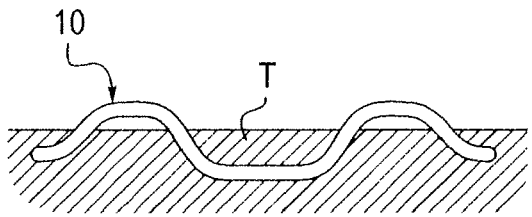
FIG. 8A-8B illustrates a shape memory element having a suture-like shape which can be stitched into the tissue.
Figure 8B:
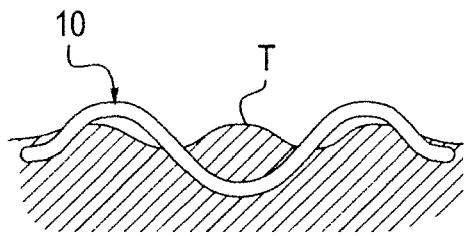

Similarly, as shown in FIG. 8A, an element 10 may have an elongate shape which is "stitched" through tissue T. Thus, portions of the element 10 lay above or on the surface of the tissue T and portions lay within the tissue T. Upon activation, the element 10 changes to its memory shape, as shown in FIG. 8B. Here, the element 10 contracts along with the associated tissue T. Such a shape memory element 10 may be used on any surface (external or internal) of the heart or related anatomy to plicate or otherwise draw tissue together. It may be appreciated that the shapes may be reversed, i.e. the original shape being the contracted shape of FIG. 8B and the memory shape being the extended shape of FIG. 8A. In such instance, the element 10 may be used to extend tissue segments.

Figure 9A:
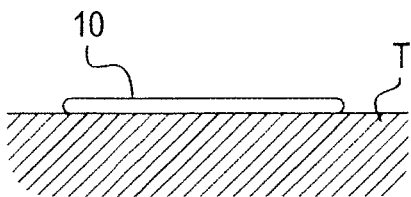
FIGS. 9A-9C illustrate shape memory elements attached to the surface of tissue.
Figure 9B:
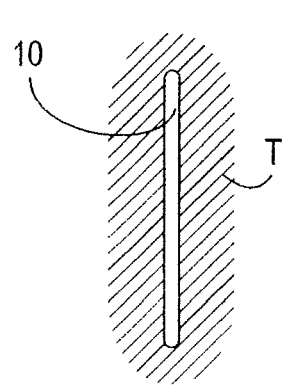
Figure 9C:
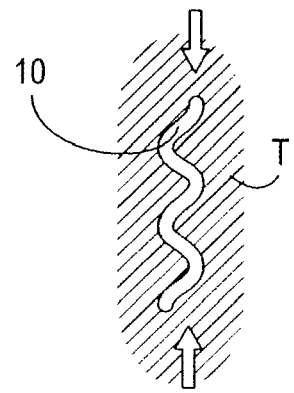

FIGS. 9A-9C illustrate shape memory elements 10 attached to the surface of tissue T. FIG. 9A provides a side view of an element 10 having a straight original shape wherein the element 10 is attached to the tissue T by any suitable mechanism or methods, such as by adhesive or suturing. FIG. 9B provides a top view of the element 10 of FIG. 9A. Upon activation, the element 10 changes to its memory shape, as shown in FIG. 9C. Here, the element 10 bends, curves or folds, contracting the associated tissue T. Such a shape memory element 10 may be used on any surface (external or internal) of the heart or related anatomy to plicate or otherwise draw tissue together. It may be appreciated that the shapes may be reversed, i.e. the original shape being the curved shape of FIG. 9C and the memory shape being the straight shape of FIGS. 9A-9B. In such instance, the element 10 may be used to extend tissue segments.

Types of Shape Memory Materials

As mentioned, a variety of shape memory materials may be used. The following types of materials are provided by way of illustration and example and should not be taken as limiting in scope of the invention.

Temperature Activated Shape Memory Metals

The shape memory elements 10 of the present invention may be comprised of shape memory metal alloys (SMAs), including Ni—Ti (Nitinol®), Cu—Zn—Al, Cu—Al—Ni and Fe—Ni—Al alloys. SMAs undergo changes in crystal structure at certain temperatures called transformation temperatures. Typically, SMAs exist in two different temperature-dependent crystal structures (phases) called martensite (lower temperature) and austenite (higher temperature or parent phase). The crystal structure of the austenite phase has a higher symmetry than the martensite phase. For example, for Cu—Al—Ni, the structure changes from cubic to orthorhombic. When a martensite SMA is heated, it begins to change into austenite. The temperature at which this phenomenon starts is called austenite start temperature (As). The temperature at which this phenomenon is complete is called austenite finish temperature (Af). When the austenite SMA is cooled, it begins to change onto martensite. The temperature at which this phenomenon starts is called martensite start temperature (Ms). The temperature at which martensite is again completely reverted is called martensite finish temperature (Mf). In addition, a rhombohedral phase is produced during cooling from the high temperature austenite phase to the low temperature martensite phase. The temperature at which this phenomenon starts is called rhombohedral start temperature (Rs) and the temperature at which this phase is completed is called rhombohedral finish temperature (Rf). Typical temperature ranges for these phases are as follows:

| | |
|---|---|
| Austenite | As = 42° C.~53° C. |
| | Af = 45° C.~70° C. |
| Rhombohedral | Rs = 30° C.~50° C. |
| | Rf = 20° C.~35° C. |
| Martensite | Ms = 10° C.~20° C. |
| | Mf = −1° C.~15° C. |

However, it may be appreciated that composition and metallurgical treatments have dramatic impacts on the above transition temperatures. In any case, the low temperature martensite structure of the SMA allows the SMA to be easily and seemingly permanently deformed. However on heating, the SMA returns to its high temperature austenite structure which is of the memory shape. Thus the material has "remembered" its shape.

Thus, a shape memory element 10 comprised of an SMA may be implanted within, partially within or attached to tissue of the heart H when in its original shape. Energy or heat is then applied to the element 10 to raise the temperature of the element 10 above its transformation temperature, such as to a temperature in the range of approximately 37° C.-70° C. This causes the element 10 to change shape to its memory shape which reconfigures the tissue. If desired, at any time, the element 10 may be cooled to below its transformation temperature to change the element 10 back to its original shape.

Ferromagnetic Shape Memory Metals

The shape memory elements 10 of the present invention may be comprised of magnetically controlled shape memory material (MSMs), including Fe—C, Fe—Pd, Fe—Mn—Si, Co—Mn, Fe—Co—Ni—Ti, $Ni_2MnGa$, Co—Ni—Al, Ni—Mn—Ga, to name a few. MSMs exhibit a paramagnetic/ferromagnetic transition besides a thermoelastic martensitic transformation. Generally, MSM material consists of internal areas, twin variants. These variants have different magnetic and crystallographic orientations. When the MSM material is subjected to a magnetic field the proportions of the variants change resulting in a shape change of the element. MSM material can be made to change shape in a variety of different ways, such as to elongate axially, bend or twist.

Thus, a shape memory element 10 comprised of an MSM may be implanted within, partially within or attached to tissue of the heart H when in its original shape. A magnetic field is then applied to the element 10 which causes the element to change shape. The magnetic field can be applied with, for example, the use of a clinically available magnetic resonance imaging (MRI) machine. Such change of shape reconfigures the associated tissue. If desired, at any time, the element 10 may be changed back to its original shape by reapplication of a magnetic field. And, since elements 10 comprised of MSMs rely on magnetic fields rather than temperature changes to change shape, the risk of overheating healthy tissue is minimized.

Examples of suitable MSMs are provided in Tellinen, J. et al. "Basic Properties of Magnetic Shape Memory Actuators," published in 8th international conference ACTUATOR 2002, Bremen, Germany, 10-12 Jun. 2002; Oikawa, et al. "Development of Co—Ni—Al-based Ferromagnetic Shape Memory Alloys," AIST Today; Vol. 1, No. 7 (2001) 18; and Cohen-Karni et al. "Fe—Pd Alloy Ferromagnetic Shape Memory Thin Films," Technion-Israel Institute of Technology in collaboration with Dr. Joost J. Vlassak and Dr. Yuki Sugimura of Harvard University, Research Experience for Undergraduates (REU), 2003, all of which are incorporated herein by reference for all purposes.

Shape Memory Polymers

The shape memory elements 10 of the present invention may be comprised of shape memory polymers (SMPs). Such SMPs may hold one shape in memory or may hold more than one shape in memory.

SMPs which hold one shape in memory are generally characterized as phase segregated linear block co-polymers having a hard segment and a soft segment. The hard segment is typically crystalline, with a defined melting point, and the soft segment is typically amorphous, with a defined glass transition temperature. Sometimes, however, the hard segment is amorphous and the soft segment is crystalline. In any case, the melting point or glass transition temperature of the soft segment is substantially less than the melting point or glass transition temperature of the hard segment. Changes in temperature cause the SMP to revert between the original shape and the memory shape.

Examples of polymers used to prepare hard and soft segments of SMPs include various polyethers, polyacrylates, polyamides, polysiloxanes, polyurethanes, polyether amides, polyurethane/ureas, polyether esters, and urethane/butadiene copolymers. For example, see U.S. Pat. Nos. 5,506,300; 5,145,935; 5,665,822, incorporated herein by reference for all purposes.

SMPs which hold more than one shape in memory may include, for example, a hard segment and at least two soft segments. The transition temperature of the hard segment is at least 10° C., and preferably 20° C., higher than the transition temperature of one of the soft segments, and the transition temperature of each subsequent soft segment is at least 10° C. and preferably 20° C. lower than the transition temperature of the preceding soft segment. Thus, an element formed from such an SMP will change shape as the temperature moves through the transition temperatures. Examples of such SMPs are described in U.S. Pat. Nos. 6,720,402 and 6,388,043, and in Lendlein, A et al. "Biodegradable, Elastic Shape-Memory Polymers for Potential Biomedical Applications", SCIENCE Vol. 296, 31 May 2002, all of which are incorporated herein by reference for all purposes. In addition, examples of such SMPs include Calo-MER™, a shape memory thermoplastic provided by The Polymer Technology Group (Berkeley, Calif.), and various shape memory polymers provided by mnemoScience GmbH (Pauwelsstraβe 19, D-52074 Aachen, and Institute for Technical and Macromolecular Chemistry, RWTH Aachen, Germany).

It may be appreciated that although these SMPs are described as changing shape in response to change in temperature, in some embodiments, the SMPs change shape in response to application of light, changes in ionic concentration and/or pH, electric field, magnetic field or ultrasound, to name a few. For example, an SMP can include at least one hard segment and at least one soft segment, wherein at least two of the segments, preferably two soft segments, are linked to each other via a functional group that is cleavable under application of light, electric field, magnetic field or ultrasound. The temporary shape is fixed by crosslinking the linear polymers. By cleaving those links the original shape can be recovered. The stimuli for crosslinking and cleaving these bonds can be the same or different.

Figure 10A:
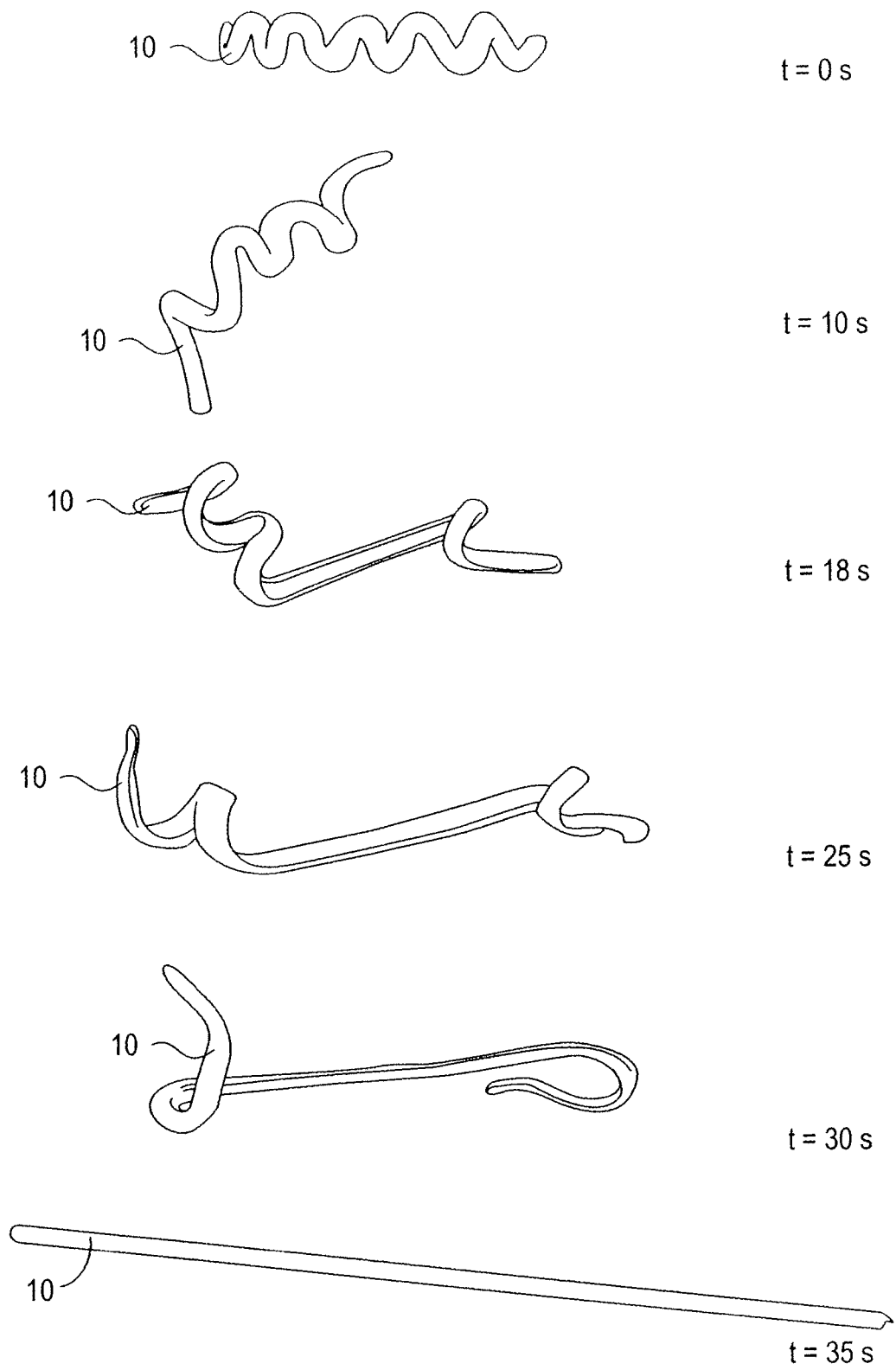
FIG. 10A illustrates a shape memory polymer transitioning between shapes.

In some instances, shape memory polymers are preferred over metallic shape memory alloys due to limitations associated with metallic shape memory alloys, such as time consuming manufacturing processes, higher manufacturing cost, high temperature treatment and limited deformation (up to 8%). Many of these limitations are resolved by using shape memory polymers. Shape memory polymers can be easily manufactured at a very low cost. In addition, the transition temperature may be easily adjusted, wherein such adjustment is more difficult with metals. Further, the polymers may be programmed into shape in seconds at about 60-70° C. and can withstand deformations of several hundred percent. In some embodiments, the entire transition occurs within 35 seconds, as illustrated in FIG. 10A which depicts the uncoiling of an SMP provided by mnemoScience GmbH.

It may be appreciated that in some embodiments the shape memory elements are biodegradable. Examples of degradable polymeric shape memory materials include poly lactic acid (PLA), poly glycolic acid (PLGA). PLA and PLGA are hydrophobic and absorbed slowly in vivo. Therefore, after 6-12 months (for example) of implantation, the heart tissue may be reshaped and the shape memory elements may be partially or completely absorbed into the body. It may also be appreciated that some metallic shape memory materials may also be biodegradable.

Coatings/Coverings

The shape memory elements 10 of the present invention may include a variety of coatings or coverings. The coatings or coverings may be present in any number and in any combination.

In some embodiments, the elements 10 are covered with a lubricious coating for ease of placement, both within a delivery device and within the tissue. Examples of lubricious coatings include polytetrafluoroethylene and coated silicone (silicone having a treated surface which provides low surface tension), to name a few.

In some embodiments, the elements 10 are covered with an anti-inflammatory coating to minimize any potential inflammatory response by the tissue. Examples of anti-inflammatory coatings include dexamethasone sodium phosphate and dexamethasone acetate, to name a few.

In some embodiments, the elements 10 are covered with a biocompatible jacket or sleeve. Such a jacket or sleeve reduces any potential immunological response by the tissue to an element 10 comprised of a less-biocompatible foreign material. Further, such a jacket or sleeve may ease removal of the element 10 from a location, such as the coronary sinus, post implant or once physical remodeling has taken place (generally within 6-12 months). In some embodiments, the biocompatible jacket or sleeve is comprised of ePTFE or Teflon®.

In some embodiments, the elements 10 are covered with a magnetic resonance imaging (MRI) absorbing coating. Such a coating may allow more focused and rapid heating of a shape memory element 10 while minimizing heat absorption by surrounding tissue. An example of such a coating is provided by Biophan Technologies, Inc. of West Henrietta, N.Y.

Similarly, in some embodiments, the elements 10 are covered with a high, medium or low intensity focused ultrasound absorbing coating or hydrogel material. Ultrasound therapy employs ultrasound transducers that are capable of delivering 1-500 W/cm$^2$, or more preferably 2-50 W/cm$^2$, at a frequency in the range of 0.5-30 MHz, to a focal spot. A portion of the energy from these high intensity sound waves is transferred to the targeted location as thermal energy. Thus, such a coating will allow more focused and rapid heating of a shape memory element 10 through its transition temperature while minimizing heat absorption by surrounding tissue. Examples of such coatings are provided by U.S. Patent Publication No. 2003/0233045 A1 and 2004/0234453 A1, incorporated herein by reference for all purposes.

Figure 10B:
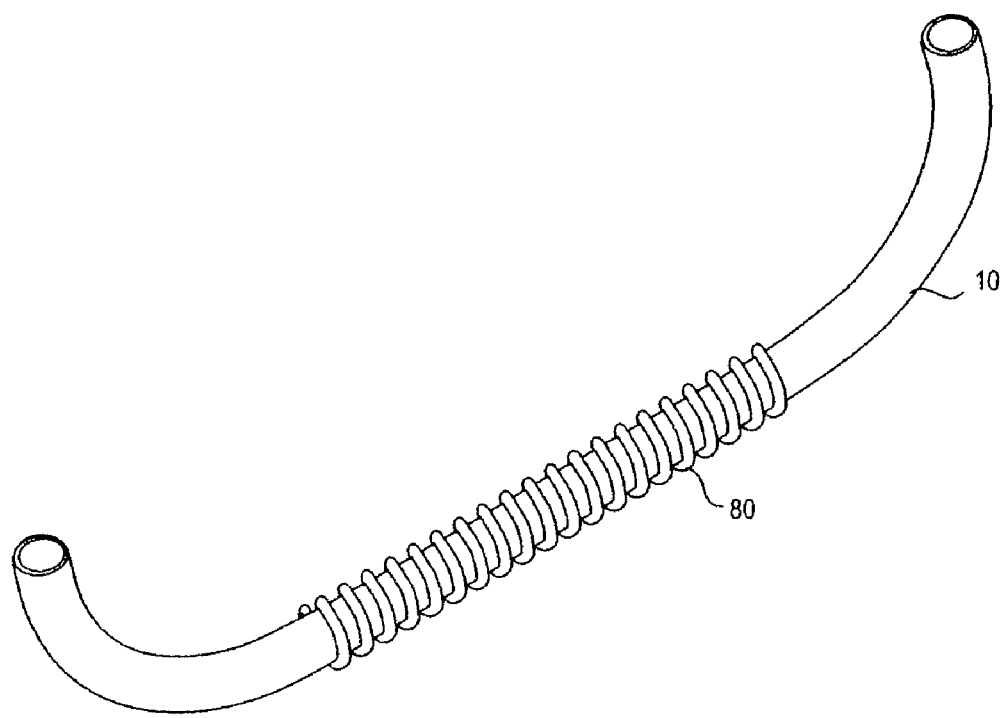
FIG. 10B illustrates an embodiment of a conductive wire wrapped around the element.

In some embodiments, the elements 10 are covered with one or more fine conductive wires 80, as illustrated in FIG. 10B. The wires 80 are wrapped around the elements 10 in any suitable configuration. FIG. 10B illustrates a single conductive wire 80 wrapped around the element 10 forming a coil shape. The one or more wires 80 may be comprised of any suitable conductive material, such as platinum coated copper, titanium, tantalum, stainless steel or gold, to name a few. The presence of the wires allow more focused and rapid heating of the shape memory element 10 while minimizing undesired heating of surrounding tissues.

In some embodiments, the elements 10 are comprised of a layers of various materials. For example, a shape memory element 10 may be comprised of a non-shape memory material (such as a metal, metal alloy or plastic) core with an outer coating of shape memory material (such as a SMA, MSM or SMP), or vice versa. Or, an element 10 may be comprised of a shape memory core with a biocompatible polymer coating. In one embodiment, the core comprises a Nitinol® rod having a length of approximately 20-40 mm and a diameter of approximately 0.25-0.5 mm. The core is coated with a thin layer of biocompatible polymer, approximately 0.1-0.3 mm thick. Examples of biocompatible polymer include polyurethane, poly tetra fluoro ethylene (PTFE), fluorinated ethylene propylene (FEP), and poly ether ether ketone (PEEK). The temperature of the core may be raised from 37° C. to a transition temperature of 45-50° C. by the application of DC current (such as DC voltage or radiofrequency) or external energy (such as a magnetic field using clinically available MRI machine or ultrasound using, for example, HIFU). The element 10 thus changes shape from the straight rod configuration to a curved, coiled or folded configuration.

In some embodiments, the elements 10 are porous or are coated with a porous coating. It may be appreciated that porous includes microporous wherein microporous materials are solids that contain interconnected pores of molecular dimensions (i.e. <2 nm). Porosity increases the surface area of the element 10 which may improve thermal conduction and heat transfer properties. Porous materials may include metals, ceramics, or polymers, to name a few. Example coatings include carbon, graphite, titanium nitrite, titanium carbite, iridium oxide and conductive porous polymers.

The elements 10 may also be used to deliver various agents, such as anti-calcification or anti-inflammatory drugs. In some embodiments, the agents are eluted from pores of a porous surface of the element 10. In other embodiments, the element 10 includes a controlled-release material impregnated with the agent, wherein the rate controlling material controls the rate at which the agent is released. Controlled-release or rate-controlled materials deliver an agent at a predetermined rate. Such delivery may be achieved by a number of methods. First, the agent may be released by diffusion through the controlled-release material. In this case, the agent is typically present as finely dispersed particles in a polymer matrix membrane. This is often termed a monolithic dispersed type system, monolithic device, or matrix diffusion system. As the concentration of agent is reduced in the matrix due to diffusion delivery, the slope of the drug diffusion curve is also reduced. The agent delivery rate decreases over time as the material is depleted. Hence, the characteristic release profile of a monolithic system follows an asymptotic curve; after an initial burst of rapid release, the elution approaches a constant rate. Second, the agent may be released by degradation of the controlled-release material. The agent may be encapsulated or contained in a biodegradable material and any number of degradation rates may be achieved by manipulating the composition of the material. Further, the agent may be released by a combination of diffusion and degradation. And, as mentioned, alternatively or in addition, the agent may be released by elution from pores. If the agent is contained in a controlled-release material which fills the pores, the agent may be released from the controlled-release material by diffusion and/or degradation and then elution from the pores themselves.

Delivery System

Figure 11A:
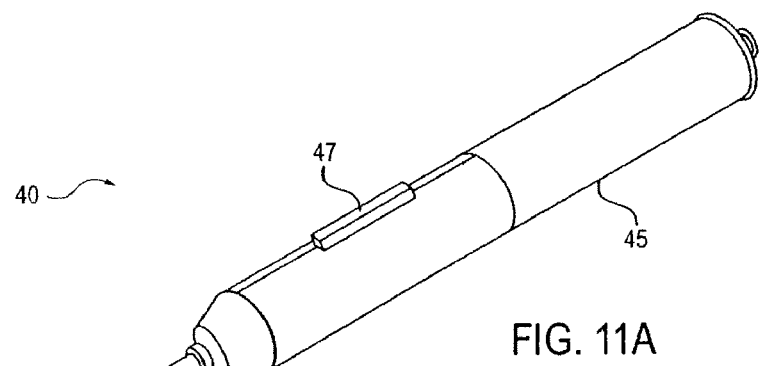
Figure 11B:
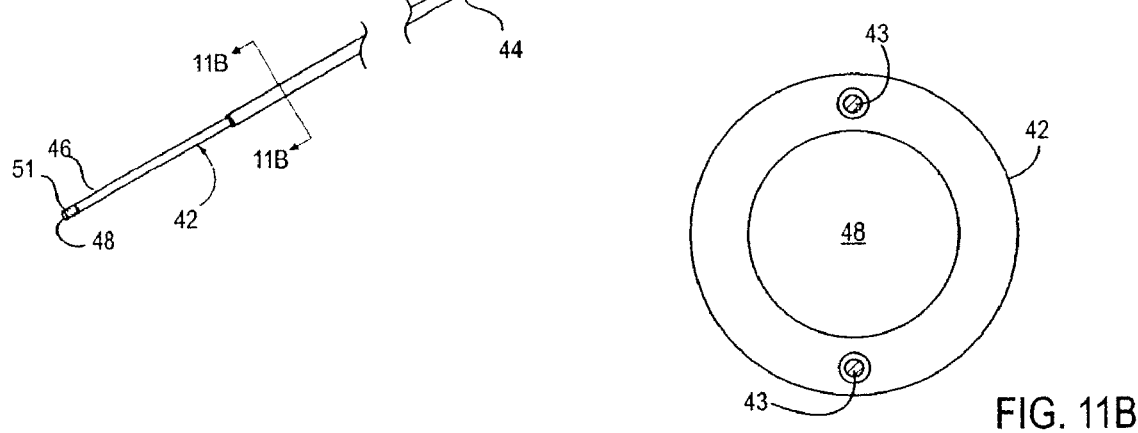

In preferred embodiments, the shape memory elements 10 are delivered to the heart wall W with the use of an endovascular delivery system. FIGS. 11A-11B illustrate an embodiment of such a delivery system 40. The system 40 includes an elongate catheter 42 having a proximal end 44 attached to a handle 45, a distal end 46, and a lumen 48 extending therethrough. In preferred embodiments, the catheter 42 has an outer diameter in the range of approximately 6-8 French. In addition, the lumen 48 may be sized for passage of a guidewire or for irrigation or contrast media injection. In some embodiments, the lumen 48 is sized for passage of a 0.018-0.035 inch guidewire; for example, the lumen 48 may have an inner diameter of approximately 0.040 inches or 1 mm. In other embodiments, the lumen 48 has an ID of 1-3 mm.

Typically, the distal end 46 includes a deflectable tip to assist in advancement of the catheter 42 through the vascular anatomy, such as from the femoral or brachial arteries. In some embodiments, the deflectable tip has a functionality similar to the deflectable tips of conventional electrophysiology or percutaneous myocardial revascularization (PMR) catheters. Advancement of the catheter 42 may be visualized with any suitable method, including fluoroscopy. Thus, in some embodiments, the catheter 42 includes a radiopaque marker 51 at the distal tip of the distal end 46. The marker 51 may be comprised of a metal such as gold or platinum. Further, the catheter 42 may be doped with radiopaque material, such as barium sulfate ($BaSO_4$).

Figures 11C, 11D:
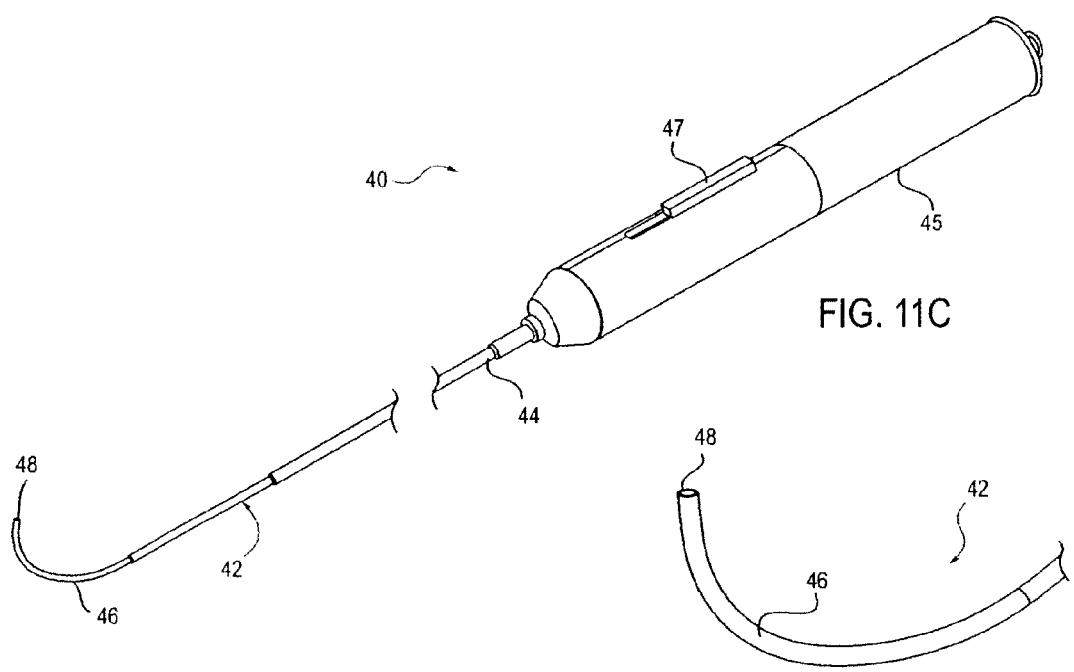

Deflection of the catheter 42 may be achieved with the use of pullwires 43. FIG. 11B illustrates a cross-section of the catheter 42 having pullwires 43 extending through walls of the catheter 42 on opposite sides of the lumen 48. The pullwires 43 are manipulated by a deflection knob 47 on the handle 45. Manipulation of the knob 47, such as retraction of the knob 47, applies tension to one of the pullwires 43, which in turn deflects the catheter 42 toward the tensioned pullwire 43, as illustrated in FIG. 11C. FIG. 11D provides a close-up illustration of the curved distal end 46 of the catheter 42. The pullwire 43 may be locked in place, holding the catheter 42 in the deflected position, or the pullwire 43 may be released by advancement of the knob 47 back to a neutral position. Further manipulation of the knob 47, such as advancement of the knob 47, applies tension to the opposite pullwire 43, which in turn deflects the catheter 42 in the opposite direction. Again, the pullwire 43 may be locked in place or released. It may be appreciated that any number of pullwires 43 may be used. Typically, the majority of the catheter 42 is comprised of material which provides sufficient flexibility to maneuver through the vascular anatomy yet sufficient stiffness for successful advancement, such as 70A-90A to 55D-75D durometer Pebax, Pellathane, polyurethane or other polymer. However, the distal end 46 of the catheter 42 is typically comprised of a more flexible material, such as 35A-60A durometer Pebax, Pellathane, polyurethane or other polymer. This difference in durometer allows deflection of the distal end 46 of the catheter 42 while maintaining relative rigidity in the remainder of the catheter 42.

Figure 11E:
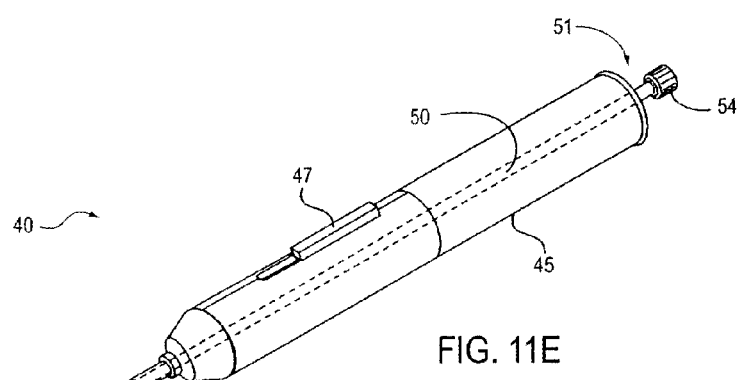
Figure 11F:
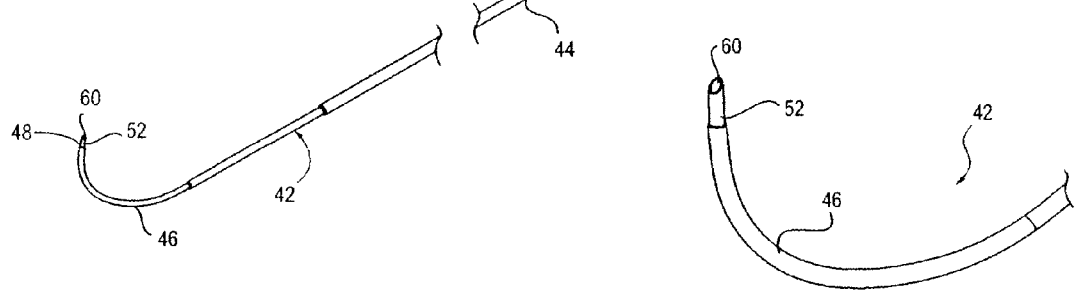

Referring to FIGS. 11E-11F, the delivery system 40 includes a needle 50 having a proximal end 51 and a needle tip 52, wherein the needle 50 which extends through the lumen 48 and is extendable and retractable within the lumen 48 by a needle advancement mechanism 54. The mechanism 54 is axially fixed in relation to the handle 45 and engages the needle 52 via threads so that rotation of the mechanism 54 axially displaces the needle 50. In preferred embodiments, the needle tip 52 is advanceable beyond the distal end 46 of the catheter 42 by a stroke distance of approximately 4-10 mm. The needle 50 may be comprised of any suitable material, such as stainless steel or Nitinol®, and may have any diameter suitable for passage through the lumen 48, such as approximately 1-3 mm.

Figures 11G, 11H:
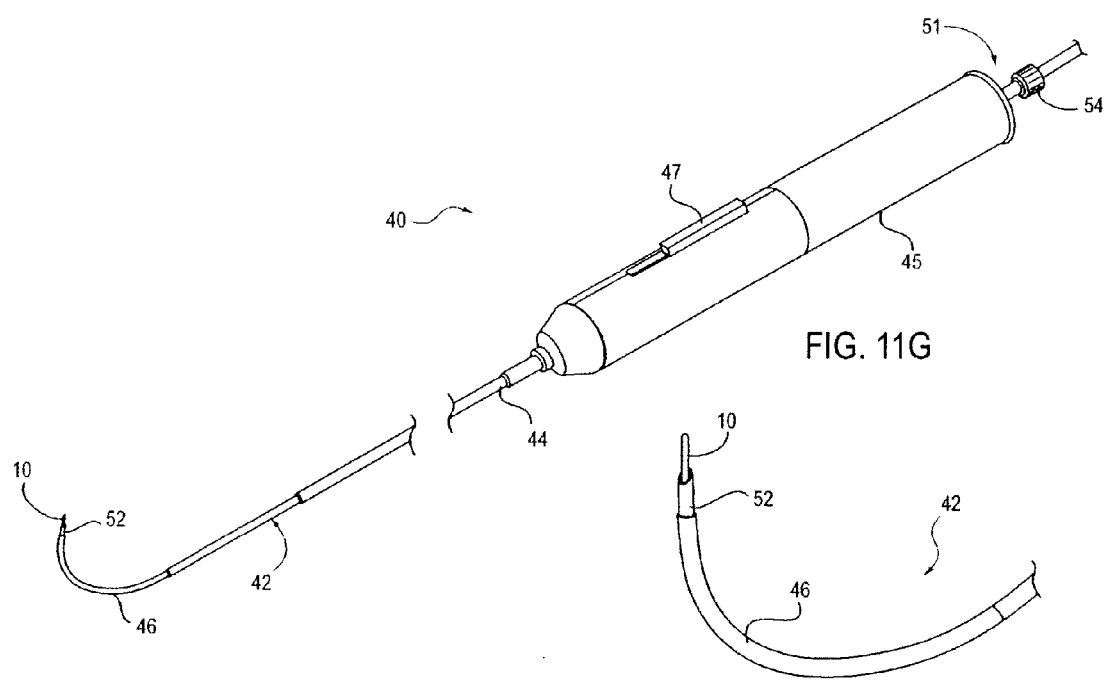

The shape memory elements 10 are loadable within the needle 50 for delivery to the heart wall W. Needle 50 has a passageway 60 extending from the proximal end 51 to the needle tip 52 so that one or more shape memory elements 10 loaded into the proximal end 51 can be advanced through the passageway 60 and expelled from the needle tip 52. The passageway 60 may have any suitable size, such as in the range of approximately 0.25-0.6 mm. In some embodiments, the passageway 60 is coated with a PTFE lining to reduce friction during advancement. Coating of the elements 10 with a biocompatible polymer, such as PTFE, also reduces friction. Referring to FIGS. 11G-11H, the elements 10 may be advanced through the passageway 60 with the use of a stylet 62. In preferred embodiments, the stylet 62 comprises an elongate shaft having a diameter sized to fit within passageway 60 and a length sized to extend from at least the distal end 51 of the needle 50 to the needle tip 52. Advancement of the stylet 62 pushes an element 10 through the passageway 60 and out of the needle tip 52, as illustrated in FIGS. 11I-11J.

Figure 12:
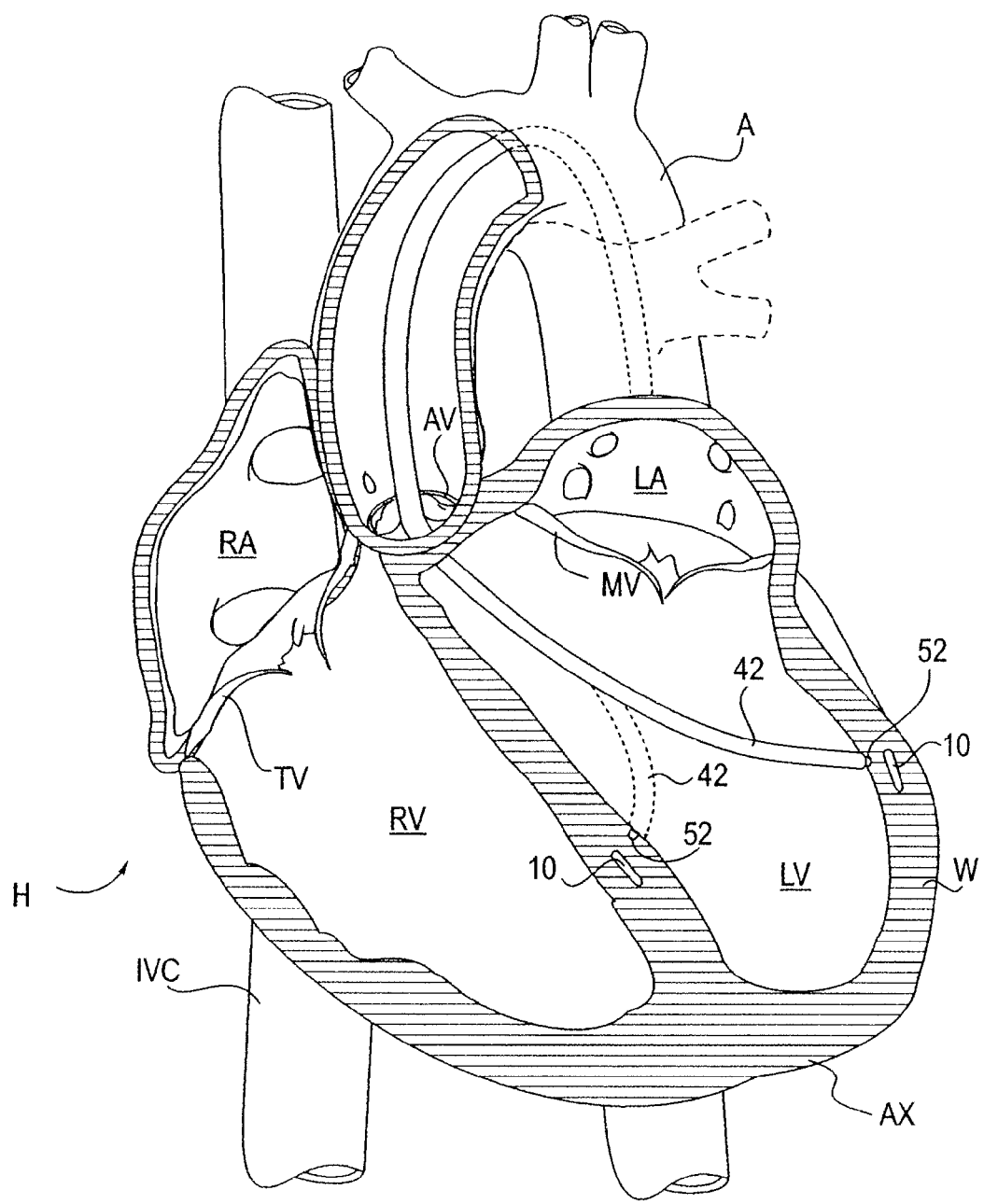
FIG. 12 illustrates an approach for endovascular delivery of shape memory elements to the walls of the left ventricle.

FIG. 12 illustrates one approach for endovascular delivery of shape memory elements 10 to the walls W of the left ventricle LV. Here, a femoral approach is shown wherein the delivery catheter 42 is advanced through the aorta A and the aortic valve AV. Typically, the catheter 42 is advanced through a sheath, such as a 9-10 French sheath, positioned within the femoral artery (not shown). Under fluoroscopy or other methods of guidance, the distal end 46 of the catheter 42 is guided within the left ventricle LV and positioned near or against the ventricular wall W at a target location. After verification of the appropriate positioning of the catheter 42, the needle tip 52 is advanced into the wall W at the target location, as illustrated in FIG. 12. One or more elements 10 are then advanced through the needle and out of the needle tip 52 so that the element(s) 10 are positioned within the wall W. The catheter 42 may then be repositioned so that the distal end 46 is disposed near or against the ventricular W at another target location, as indicated by dashed image of the catheter. Thus, one or more elements 10 may be positioned at other target locations around the left ventricle LV. This may be repeated any number of times.

It may be appreciated that the left ventricle LV may alternatively be approached by advancement of the catheter 42 through the inferior vena cava IVC, into the right atrium RA, across the interatrial septum, into the left atrium LA and through the mitral valve MV. Similarly, the right ventricle RV may be approached through the inferior vena cava IVA, into the right atrium RA and through the tricuspid valve TV. A variety of other endovascular approaches may also be used. It may also be appreciated that non-endovascular approaches may also be used wherein the shape memory elements 10 are placed on or within the walls W by open chest surgery or through minimally invasive procedures where access is achieved thorascopically.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A device for reshaping heart anatomy comprising:
   a shape memory material which is transitionable between an original shape and at least one memory shape, wherein the original shape is configured for at least partial implantation within a tissue area of the heart anatomy and the at least one memory shape is configured to apply force to the tissue area in a manner which reshapes the heart anatomy; and
   an energy absorbing material covering the shape memory material, the energy absorbing material configured to generate thermal energy when exposed to an external energy source and to transfer the thermal energy to the shape memory material to activate the transition between the original shape and the at least one memory shape.

2. A device as in claim 1, wherein the shape memory material undergoes a deformation of at least 50% in the transition.

3. A device as in claim 1, wherein the transition substantially occurs within up to approximately 5-120 seconds.

4. A device as in claim 1, wherein the at least one memory shape has a more curved configuration than the original shape.

5. A device as in claim 1, wherein the tissue area is located within a wall of a ventricle and wherein the at least one memory shape is configured to apply force to the tissue area in a manner which reduces a width of the ventricle.

6. A device as in claim 1, wherein the tissue area is located within the left atrium wall and wherein the at least one memory shape is configured to apply force to the tissue area in a manner which reshapes an annulus of a mitral valve.

7. A device as in claim 1, wherein the shape memory material comprises at least one shape memory metal or metal alloy.

8. The device as in claim 1, wherein the energy absorbing material comprises a magnetic resonance imaging (MRI) absorbing material.

9. The device as in claim 1, wherein the energy absorbing material comprises an ultrasound absorbing material.

10. The device as in claim 1, wherein the energy absorbing material comprises at least one fine conductive wire.

11. A method of reshaping heart anatomy comprising:
    providing an implant device comprising:
      a shape memory material which is transitionable between an original shape and at least one memory shape; and
      an energy absorbing material covering the shape memory material;
    implanting the implant device, with the shape memory material having its original shape, at least partially within a tissue area of the heart anatomy; and
    applying energy from the external energy source to the implant device to generate thermal energy in the energy absorbing material and to transfer the thermal energy from the energy absorbing material to the shape memory material,
    wherein transferring the thermal energy from the energy absorbing material to the shape memory material activates the shape memory material causing transition from its original shape to one of the at least one memory shapes while the implant device is at least partially implanted, wherein the transition causes the tissue area to move in a manner which reshapes the heart anatomy.

12. A method as in claim 11, wherein the tissue area is located within a wall of a ventricle and reshaping the heart anatomy comprises reducing a width of the ventricle.

13. A method as in claim 11, wherein implanting comprises positioning the implant device at least partially on a surface of the heart anatomy.

14. A method as in claim 13, wherein implanting comprises stitching the implant device through the tissue area.

* * * * *